US007632523B2

(12) United States Patent
Ramirez et al.

(10) Patent No.: US 7,632,523 B2
(45) Date of Patent: Dec. 15, 2009

(54) ENHANCED ACTIVITY HYDROGEN PEROXIDE DISINFECTANT

(75) Inventors: Jose A. Ramirez, Vernon Hills, IL (US); Navid Omidbakhsh, Mississauga (CA)

(73) Assignee: Virox Technologies Inc., Oakville, Ontario (CA)

( * ) Notice: Subject to any disclaimer, the term of this patent is extended or adjusted under 35 U.S.C. 154(b) by 0 days.

(21) Appl. No.: 11/518,188

(22) Filed: Sep. 11, 2006

(65) Prior Publication Data

US 2007/0059380 A1      Mar. 15, 2007

Related U.S. Application Data

(63) Continuation of application No. 10/364,348, filed on Feb. 12, 2003, now abandoned.

(60) Provisional application No. 60/355,753, filed on Feb. 12, 2002.

(51) Int. Cl.
A01N 59/00      (2006.01)
A01N 31/04      (2006.01)
A01N 25/22      (2006.01)
A01N 41/04      (2006.01)

(52) U.S. Cl. .................. 424/616; 424/DIG. 6; 514/557; 514/558; 514/559; 514/560; 514/574; 514/576; 514/578; 514/709; 514/711; 514/730; 514/970; 504/151

(58) Field of Classification Search .................. 424/616, 424/DIG. 6; 514/730, 970
See application file for complete search history.

(56) References Cited

U.S. PATENT DOCUMENTS

| | | | |
|---|---|---|---|
| 3,969,258 A | 7/1976 | Carandang et al. |
| 4,051,058 A | 9/1977 | Bowing et al. |
| 4,051,059 A | 9/1977 | Bowing et al. |
| 4,405,482 A | 9/1983 | Hayes et al. |
| 4,446,153 A | 5/1984 | Yang |
| 4,477,438 A | 10/1984 | Willcockson et al. |
| 4,518,585 A | 5/1985 | Greene et al. |
| 4,525,291 A | 6/1985 | Smith et al. |
| 4,525,292 A | 6/1985 | Cushman et al. |
| 4,557,898 A | 12/1985 | Greene et al. |
| 4,637,899 A | 1/1987 | Kennedy, Jr. |
| 4,878,951 A | 11/1989 | Pochard et al. |
| 5,059,417 A | 10/1991 | Williams et al. |
| 5,149,463 A | 9/1992 | Peterson |
| 5,171,564 A | 12/1992 | Nathoo et al. |
| 5,200,189 A | 4/1993 | Oakes et al. |
| 5,205,960 A | 4/1993 | Kristopeit et al. |
| 5,244,593 A | 9/1993 | Roselle et al. |
| 5,264,229 A | 11/1993 | Mannig et al. |
| 5,387,605 A | 2/1995 | Beilfuss et al. |
| 5,523,012 A | 6/1996 | Winterton et al. |
| 5,599,400 A | 2/1997 | Mao et al. |
| 5,602,090 A | 2/1997 | Melikyan et al. |
| 5,641,530 A | 6/1997 | Chen |
| 5,718,910 A | 2/1998 | Oakes et al. |
| 5,723,400 A | 3/1998 | Morini et al. |
| 5,723,406 A | 3/1998 | Larose et al. |
| 5,736,498 A | 4/1998 | Gray |
| 5,736,582 A | 4/1998 | Devillez |

(Continued)

FOREIGN PATENT DOCUMENTS

CA         1102502         6/1981

(Continued)

OTHER PUBLICATIONS

MGC Baldry, "The Bactericidal, Fungicidal and Sporicidal Properties of Hydrogen Peroxide and Peractetic Acid", 1982, Journal of Applied Bacteriology 54, 417-423.

(Continued)

Primary Examiner—John Pak
(74) Attorney, Agent, or Firm—Clark & Brody

(57) ABSTRACT

An enhanced activity aqueous disinfecting solution having a pH of from about 0.5 to about 6 and consisting essentially of (i) hydrogen peroxide in a concentration of from about 0.05 to about 8 w/w % of the solution; (ii) at least one anionic surfactant selected from the group consisting of C8 to C16 alkyl aryl sulfonic acids and alkali metal, ammonium, ethanolamine, calcium and magnesium salts thereof, sulfonated C12 to C22 carboxylic acids and alkali metal, ammonium, calcium and magnesium salts thereof, C6 to C22 alkyl diphenyl oxide sulfonic acids and alkali metal, ammonium, ethanolamine, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkali metal, ammonium, calcium and magnesium C8 to C18 alkyl sulfates, alkyl or alkenyl esters or diesters of sulfosuccinic acid in which the alkyl or alkenyl groups independently contain from six to eighteen carbon atoms and alkali metal, ammonium, calcium and magnesium salts thereof, and mixtures thereof, in a concentration range of from about 0.02 to about 8 w/w % of the solution. Optionally, the solution may contain (iii) at least one additional ingredient chosen from a monocarboxylic acid, a polycarboxylic acid, and mixtures thereof, in a concentration of from about 0.05 to about 4 w/w % of the solution; and (iv) at least one further additional ingredient chosen from benzyl alcohol, an alcohol comprising one to six carbon atoms, and mixtures thereof, in a concentration of from about 0.1 to about 10 w/w % of the solution.

25 Claims, 3 Drawing Sheets

U.S. PATENT DOCUMENTS

| | | | |
|---|---|---|---|
| 5,827,542 A | 10/1998 | Miner et al. | |
| 5,855,217 A | 1/1999 | John | |
| 5,891,392 A | 4/1999 | Monticello et al. | |
| 5,900,256 A | 5/1999 | Scoville, Jr. et al. | |
| 6,043,209 A | 3/2000 | Micciche et al. | |
| 6,096,348 A | 8/2000 | Miner et al. | |
| 6,110,883 A | 8/2000 | Petri et al. | |
| 6,296,880 B1 | 10/2001 | Murad | |
| 6,346,279 B1 | 2/2002 | Rochon | |
| 6,383,523 B1 | 5/2002 | Murad | |
| 6,444,636 B1 | 9/2002 | Toussaint et al. | |
| 6,479,454 B1 | 11/2002 | Smith et al. | |
| 6,593,283 B2 | 7/2003 | Hei et al. | |
| 6,617,294 B2 | 9/2003 | Narula et al. | |
| 6,627,589 B1 | 9/2003 | Arvanitidou | |
| 6,841,090 B1 | 1/2005 | Allighieri et al. | |
| 6,927,237 B2 | 8/2005 | Hei et al. | |
| 7,354,604 B2 * | 4/2008 | Ramirez et al. | 424/616 |
| 2002/0072288 A1 | 6/2002 | Hei et al. | |
| 2002/0168422 A1 | 11/2002 | Hei et al. | |
| 2003/0161891 A1 | 8/2003 | Ruiter | |
| 2003/0181377 A1 | 9/2003 | Hallahan et al. | |
| 2003/0203035 A1 | 10/2003 | Hasan et al. | |
| 2003/0206965 A1 | 11/2003 | Hasan et al. | |
| 2003/0228996 A1 | 12/2003 | Hei et al. | |
| 2004/0033923 A1 | 2/2004 | McClung | |
| 2004/0137077 A1 | 7/2004 | Ancira et al. | |
| 2004/0171687 A1 | 9/2004 | Kemp et al. | |
| 2004/0182793 A1 | 9/2004 | Owens | |
| 2005/0019421 A1 | 1/2005 | Hobbs et al. | |
| 2005/0058719 A1 | 3/2005 | Ramirez et al. | |
| 2005/0133460 A1 | 6/2005 | McClung | |
| 2005/0145824 A1 | 7/2005 | McClung | |
| 2005/0145825 A1 | 7/2005 | McClung | |
| 2005/0145826 A1 | 7/2005 | McClung | |
| 2005/0255172 A1 | 11/2005 | Omidbakhsh | |
| 2006/0172911 A1 | 8/2006 | McClung | |

FOREIGN PATENT DOCUMENTS

| | | |
|---|---|---|
| CA | 1244759 | 11/1988 |
| DE | 2629081 | 6/1976 |
| DE | 3229097 A1 | 8/1982 |
| DE | 3543500 A1 | 12/1985 |
| EP | 0057153 | 1/1982 |
| EP | 0 127 557 | 12/1984 |
| EP | 0087049 | 11/1986 |
| EP | 252278 | 6/1987 |
| EP | 0289463 | 4/1988 |
| EP | 0351772 A2 | 7/1989 |
| EP | 0351772 A3 | 7/1989 |
| EP | 456272 A1 | 5/1991 |
| EP | 0524150 | 7/1992 |
| EP | 0505935 A1 | 9/1992 |
| EP | 0 517 996 | 12/1992 |
| EP | 0582359 A1 | 7/1993 |
| EP | 0582360 | 7/1993 |
| EP | 0582360 A1 | 7/1993 |
| EP | 776613 A1 | 6/1997 |
| EP | 0845526 | 11/1997 |
| EP | 1369037 A1 | 5/2003 |
| EP | 1374679 A2 | 1/2004 |
| GB | 1584170 | 2/1981 |
| GB | 2101350 | 5/1982 |
| JP | 5712302 | 8/1982 |
| JP | 987677 | 3/1997 |
| JP | 10121097 | 5/1998 |
| JP | 10130693 | 5/1998 |
| WO | 93/04664 | 3/1993 |
| WO | 93/14183 | 7/1993 |
| WO | 95/04001 | 2/1995 |
| WO | 96/20737 | 7/1996 |
| WO | 97/28691 | 8/1997 |
| WO | 98/11777 | 3/1998 |
| WO | 98/18894 | 5/1998 |
| WO | 98/21305 | 5/1998 |
| WO | 98/59028 | 12/1998 |
| WO | 99/02368 | 1/1999 |
| WO | 99/03446 | 1/1999 |
| WO | 99/27066 | 6/1999 |
| WO | 00/27981 | 5/2000 |
| WO | 02/055647 A1 | 7/2002 |
| WO | WO03/005817 A2 | 1/2003 |
| WO | WO03/005818 A1 | 1/2003 |
| WO | 03/067989 | 8/2003 |
| WO | 03/076560 A1 | 9/2003 |
| WO | 2004/035718 A2 | 4/2004 |
| WO | WO2004/045281 A2 | 6/2004 |

OTHER PUBLICATIONS

Milton E. Parker & John H. Litchfield, Food Plant Sanitation: Effective Detergency and Cleaning Practice, (New York: Reinhold Publishing Corporation, 1962).

"Announcement" (1999), vol. 14, No. 1, The Canadian Journal of Infection Control.

Disinfection, Sterilization, and Preservation, 4th Edition, Seymour S. Block, Lea & Febiger 1991 pp. 167-172, 178-181, 263-271.

Dowfax™ Hydrotope Solution.

Lopes, J.A., "Evaluation of dairy and foot plant sanitizers against salmonella typhimurium and listeria monocytogenes", J. Dairy Sci., 69, 2791-2796.

Sattar et al., "A product based on accelerated and stabilized hydrogen peroxide, evidence for broad-spectrum germicidal activity", Can. J. Infection Control, Winter 1998.

Database WPI, Section Ch, Week 199615, Derwent Publication Ltd., London, GB; Class D22, AN 1996-149587, XP002287351.

G.R. Dychdala et al., Surface-Active Agents: Acid-Anionic Compounds, pp. 256-262; XP-002287349.

Database Chemabs 'Online! Chemical Abstracts Service, Columbus, OH, US; XP002287350; retrieved from STN-International Database accession No. 136:351642—abstract.

Database WPI, Section Ch, Week 199918, Derwent Publications Ltd., London, GB; Class C03, AN 1999-205420, XP002287352.

XP-002287351: "BIOL INSTR MRF RES INST"; Database WPI published by Derwent Publications Ltd.; abstract only; c. Jul. 27, 1995.

XP-002287352: "(Wang-I) Wang L"; Database WPI published by Derwent Publications Ltd.; abstract only; c. Dec. 16, 1998.

XP-002287349: "Surface-Active Agents: Acid-Anionic Compounds" by G. R. Dychdala et al.; *Disinfection, Sterilization and Preservation*; c. 1991.

XP-001187350: "Salicyclic Acid"; published by Database Chemabs Online Chemical Abstract Service; abstract only; c. May 30, 2002.

* cited by examiner

ENHANCED ACTIVITY HYDROGEN PEROXIDE DISINFECTANT

This application is a continuation of U.S. application Ser. no. 10/364,348, filed on Feb. 12, 2003, now abandoned, which claims the benefit of U.S. provisional application Ser. No. 60/355,753, filed on Feb. 12, 2002 under 35 U.S.C. section 119(e).

FIELD OF THE INVENTION

The present invention relates to disinfectants and, in particular, it relates to hydrogen peroxide solutions with improved disinfectant and antimicrobial properties.

BACKGROUND TO THE INVENTION

In the past few years, efforts have been concentrated on developing chemicals that will be highly effective against microorganisms when highly diluted, will be low in toxicity to humans and other animals, and will not injure the environment. Of the known disinfectants and antimicrobials, hydrogen peroxide appears to have exceptional potential, especially in terms of toxicity and injury to the environment, because the decomposition products, water and oxygen, are benign. Also, it tends to have broad spectrum antimicrobial activity. Broad spectrum activity is important in situations where harmful organisms are present but their identity is not known. Hydrogen peroxide based disinfectants are useful in many different applications, including in hospitals, clinics, laboratories, dental offices, home care and chronic care facilities. They may also be used in food and beverage processing and preparation, animal husbandry, the hospitality industry and for general sanitation, e.g. janitorial services.

In order to provide fast, effective action, prior art disinfectant solutions have had to employ relatively high concentrations of hydrogen peroxide. At higher concentrations, the solutions may not be practical or economically viable, may be subject to hazardous goods regulations, and may require special precautions for handling and use. For example, at concentrations of above about 8 w/w % aqueous solution, hydrogen peroxide is considered corrosive, more so at higher concentrations, and is also a strong oxidizing agent. Solutions containing less than about 8 w/w % hydrogen peroxide are preferred for their improved safety profile. At concentrations of 1-3 w/w % aqueous solution, hydrogen peroxide is considered non-corrosive and non-irritating; at concentrations of 3-7 w/w % aqueous solution, hydrogen peroxide is considered non-corrosive but an eye irritant.

Heretofore, one of the major drawbacks of hydrogen peroxide, in very low concentrations, is that its antimicrobial action is too slow. For example, prior art references indicate that a 0.1 w/w % aqueous solution of hydrogen peroxide requires 60 minutes to disinfect surfaces contaminated with *staphylococcus aureus*, whereas a 25.8 w/w % aqueous solution of hydrogen peroxide requires only 20 seconds. The latter solution is clearly unacceptable from both commercial and economic standpoints.

Attempts have been made to improve the efficacy of low concentration hydrogen peroxide disinfecting solutions. For example, Winterton et al. discloses, in U.S. Pat. No. 5,523,012, a hydrogen peroxide disinfecting solution for contact lenses buffered to a pH of about 6.9 and which has from about 0.1 w/w % to about 1.0 w/w % of an ocularly compatible surfactant. In one experiment, the addition of about 0.4% anionic sulfosuccinate surfactant improved the killing time for *aspergillus fumigatus* to 6.9 minutes, compared to 12.3 minutes for a solution containing no added surfactant. However, even 6.9 minutes is far too long for many applications.

U.S. Pat. No. 5,264,229 to Mannig et al teaches a process of extending the shelf life of commercially processed food products, such as poultry, fowl and seafood products by contacting the food products with a sufficient amount of food grade hydrogen peroxide and food grade surface active agent selected from the group consisting of alkyl aryl sulfonates, sulfates, sulfonates of fatty acids, sulfates of alcohols and sulfosuccinates. The hydrogen peroxide and surface active agent are present in chiller water in which the food products are immersed and serve to remove and reduce the number of bacteria on the surface of the food products. Up to 1 w/w % hydrogen peroxide and from 5 to 100 ppm surface active agent are used in the chiller water. The solutions of Mannig et al are able to achieve only moderate levels of disinfectant activity using a 45 minute contact time. While the Mannig solution may be sufficient for preserving foods, it is inadequate for short contact time disinfection.

Hydrogen peroxide is a compound which is highly susceptible to decomposition by the presence of dissolved impurities, mostly transition metal cations. Impurities causing hydrogen peroxide decomposition are typically contained in either the water used in preparation of a commercial disinfectant from an aqueous hydrogen peroxide stock, or in the additional ingredients of the formulation (i.e. surfactants, builders, etc.). The most effective method for preventing decomposition of the hydrogen peroxide is by sequestration or chelation of the dissolved catalytic metal species, typically through the use of phosphate or phosphonate compounds. The increased product shelf life gained by the use of phosphorus stabilizers has allowed the commercial, albeit limited, use of such compositions.

Most if not all peroxygen-based mixtures used for cleaning and disinfection discussed in the prior art either suffer from impracticably long contact times, unfeasibly high hydrogen peroxide concentrations or contain at least one type of phosphorus compound in non-trace quantities. Although the role of phosphorus in the eutrophication of lakes and rivers due to artificial sources is still a matter of debate, many regions in the world have imposed severe restrictions on the amount of phosphorus that can be discharged into storm and sanitary sewers.

In certain situations, it is therefore desirable to provide a complex multicomponent hydrogen peroxide solution with the capability of disinfection at short contact times, has low non-hazardous concentrations of ingredients, and which contains no phosphorus-based materials.

Though the prior art is replete with hydrogen peroxide containing disinfectants, the present invention is intended to provide an improved hydrogen peroxide disinfectant having enhanced activity to permit rapid and effective disinfection of hard surfaces and skin of humans and animals with a hydrogen peroxide concentration as low as 0.5 w/w %. Select embodiments of the present invention do not contain any added phosphorus-based materials other than those naturally present in commercial hydrogen peroxide stock solutions, which are present in quantities permitted in jurisdictions which impose restrictions on phosphorus discharge into the environment.

SUMMARY OF THE INVENTION

Figure 1:
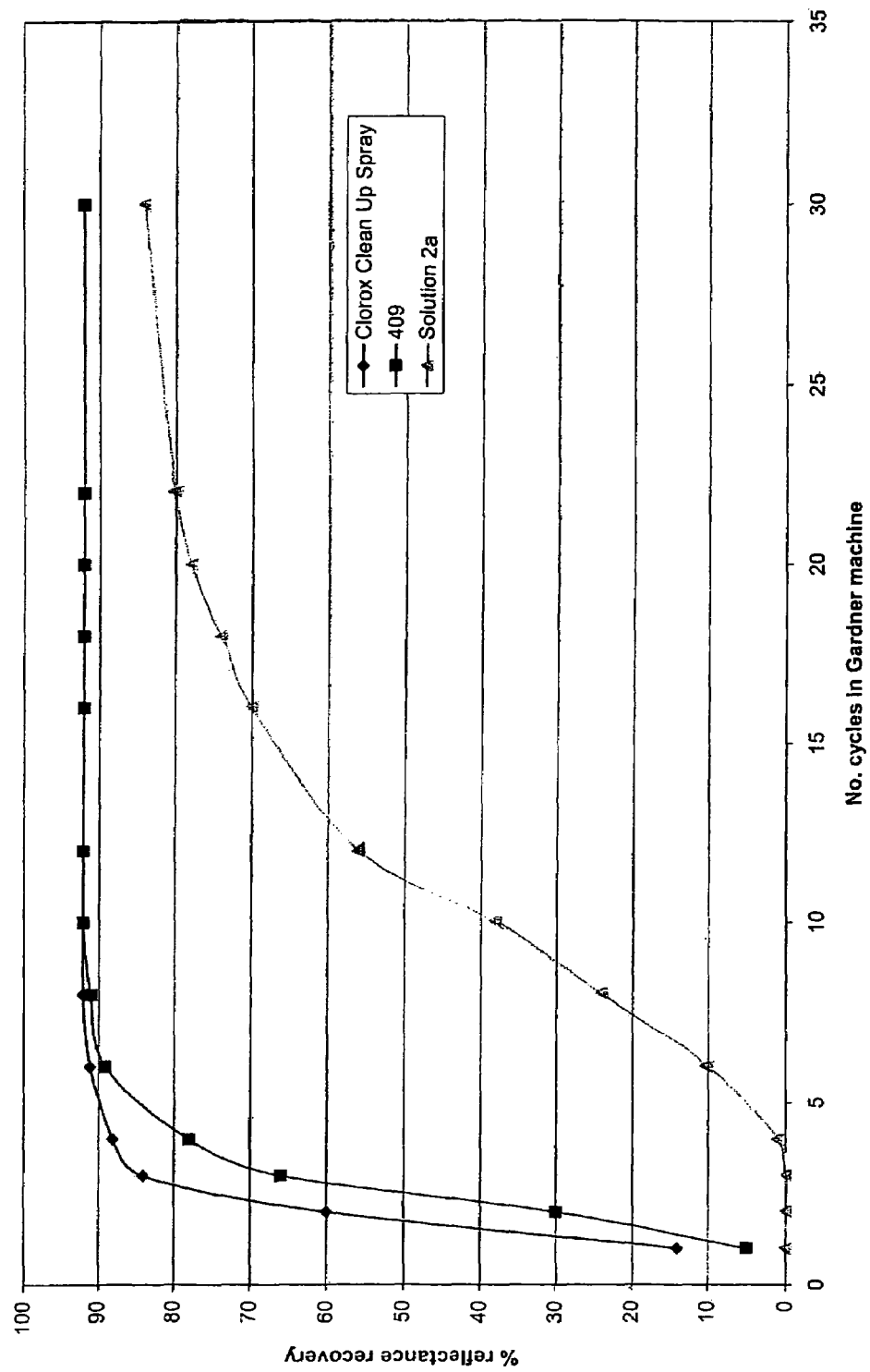
FIG. 1 is a graphical illustration of the cleaning efficiency of Solution 2a, according to one embodiment of the present invention, tested as described in Example 2 below against commercial formulations.

It has now been found that the addition of certain anionic surfactants in certain concentrations greatly, and surprisingly, enhances the bactericidal and/or virucidal activity of aqueous acidic hydrogen peroxide solutions. Furthermore, by the careful selection of the components in the mixture, solutions of commercially acceptable stability and cleaning ability can be achieved without the use of phosphorus containing stabilizers.

In accordance with a first aspect, the invention provides a ready-to-use, aqueous disinfecting solution, having a pH of from about 0.5 to about 6, and consisting essentially of:

i) hydrogen peroxide in a concentration of from about 0.05 to about 8 w/w % of the total solution; and ii) at least one anionic surfactant chosen from C8 to C16 alkyl aryl sulfonic acids and alkali metal, ammonium, ethanolamine, calcium and magnesium salts thereof; sulfonated C12 to C22 carboxylic acids and alkali metal, ammonium, calcium and magnesium salts thereof; C6 to C22 alkyl diphenyl oxide sulfonic acids and alkali metal, ammonium, calcium and magnesium salts thereof; naphthalene sulfonic acids and alkali metal, ammonium, calcium and magnesium salts thereof; C8 to C22 alkyl sulfonic acids and alkali metal, ammonium, calcium and magnesium salts thereof; alkali metal, ammonium, calcium and magnesium C8 to C18 alkyl sulfates; alkyl or alkenyl esters or diesters of sulfosuccinic acids in which the alkyl or alkenyl groups independently contain from six to eighteen carbon atoms and alkali metal, ammonium, calcium and magnesium salts thereof; and mixtures thereof; in a concentration of from about 0.02 to about 8 w/w % of the total solution.

The concentration of the hydrogen peroxide may be from about 0.05, 0.1, 0.45, or 0.5 w/w/ % of the total solution. Also, it may be up to about 4, 2.5, 2, 1.2, or 1 w/w % of the total solution. Preferably, the concentration is from about 0.5 to 1.2 w/w %.

The concentration of anionic surfactant may be from about 0.05 or 0.8 and up to about 6, 5, 4, 3.6, 2 or 1 w/w % of the total solution.

Furthermore, the pH of ready-to-use solutions may be from about 0.7, 1.0, 1.5, 2, or 2.5 to about 4.5, 4.0, 3.5, 2.5, or 2 w/w % of the total solution, and preferably from about 1 to about 4. In the case of hard surface disinfectants, the pH is more preferably from about 1.5 to about 3.5, while in the case of topical disinfectants, the pH is more preferably from about 2.5 to about 4.5. Preferred concentrate versions of these solutions have pH values ranging from about 0.7 to about 2. To achieve the preferred pH values, buffering or other pH adjusting agents may be added to the solution. These agents include organic and inorganic acids or bases such as phosphoric acid, citric acid, sulfuric acid, sodium hydroxide and potassium hydroxide, the latter being otherwise known as caustic potash.

The anionic surfactant is preferably chosen from dodecyl benzene sulfonic acid and alkali metal, ammonium, ethanolamine, calcium and magnesium salts thereof; C6 to C22 alkyl diphenyl oxide sulfonic acids and alkali metal, ammonium, calcium and magnesium salts thereof; ethoxylated dodecyl sulfosuccinates, dioctyl sulfosuccinates, ethoxylated dodecyl sulfosuccinates, and mixtures thereof. More preferably, the anionic surfactant is chosen from dodecyl benzene sulfonic acid and an alkali metal salt thereof, C6 alkylated sulfonated diphenyl oxide disodium salt, disodium dioctyl sulfosuccinate, sodium lauryl sulfate, ammonium lauryl sulfate, disodium lauryl ether sulfosuccinate ethoxylated to 3 moles of ethylene oxide, and mixtures thereof.

Embodiments for use in topical applications (e.g. formulations to be applied to the skin of humans or animals) should contain those anionic surfactants which are mild to the skin, including disodium dioctyl sulfosuccinate, sodium lauryl sulfate, ammonium lauryl sulfate, disodium lauryl ether sulfosuccinate ethoxylated to 3 moles of ethylene oxide, and mixtures thereof.

To further enhance the germicidal efficacy of the solution, the solution may contain at least one additional ingredient chosen from a monocarboxylic acid (e.g. acetic acid and glycolic acid), a polycarboxylic acid (e.g. citric acid), benzyl alcohol, an alcohol comprising one to eight carbon atoms (e.g. propylene glycol n-propyl ether, ethylene glycol n-propyl ether, methanol, ethanol, iso-propanol, n-butanol and n-pentanol), and mixtures thereof. Preferred alcohols are the short chain (i.e. C1-C6) alcohols and benzyl alcohol. The carboxylic acids have known pH buffering, stabilizing and cleaning properties and are preferably present in a total concentration of from about 0.1 to about 10 w/w %, more preferably from about 0.05 to about 4.0 w/w % of the solution. Preferred monocarboxylic acids are glycolic acid and acetic acid. A preferred polycarboxylic acid is citric acid.

The alcohol is preferably present in a total concentration of from about 0.1 to about 10 w/w % of the total solution. In the case of topical solutions, the alcohol is preferably present in a concentration of from about 2 to about 5 w/w % so that the solution does not give rise to excessive drying and irritation. The recited alcohols are believed to also provide additional cleaning performance in respect of organic contaminants.

In accordance with a second aspect, the invention provides a concentrated aqueous hydrogen peroxide solution which can be diluted with water to produce a ready-to use solution according to the first aspect. Accordingly, the concentration of the ingredients of the solution may be much higher than as stated above. For example, the hydrogen peroxide concentration may be as high as 20 w/w %. Similarly, the anionic surfactant concentration may be as high as 10 w/w %. If the diluent is regular tap water which will likely contain metal cations and other impurities serving to increase the rate of hydrogen peroxide decomposition, hydrogen peroxide stabilizers may be included in the solution. These will be described further below.

The invention also provides, in accordance with a third aspect, a solid disinfectant formulation which can be dissolved in water to produce a ready-to-use solution according to the first aspect. It will be clear to the person skilled in the art how to manufacture such a solid formulation. In such embodiments, the formulation comprises at least one hydrogen peroxide releasing component, which may be chosen from sodium percarbonate, sodium perborate monohydrate, and sodium perborate tetrahydrate. Preferably, the component is sodium percarbonate or sodium perborate. The anionic surfactants would be present either in salt form or in acid form, as will be apparent to the person skilled in the art.

Depending on the application, the present solution and solid formulation may contain the following additional optional ingredients which do not alter the basic and novel properties thereof. The basic and novel properties are defined herein to mean the bactericidal and/or virucidal activity of the solution and solid formulation. The total amount of these optional ingredients generally will not exceed 10 w/w % of the final, total, ready-to-use solution and often will not exceed about 7 w/w %. In solid embodiments of the invention, bulking agents may be included and, in such case, the total amount of optional ingredients may exceed 10 w/w % of the final, total, ready-to-use solution.

To improve stability of the solution, hydrogen peroxide stabilizers may be added. In jurisdictions which do not impose restrictions on phosphorus emissions, these stabilizers may be based on phosphorus. These include: 1-hydroxyethylidene-1,1-diphosphonic acid, amino tri(methylene phosphonic acid), 2-hydroxyethylimino tri(methylene phosphonic acid), ethylene diamine tetra(methylene phosphonic acid), phosphoric acid, and sodium tripolyphosphate. As well, foam generating or stabilizing ingredients, emulsifiers, hydrotropes, and detergents may be included. Emulsifiers and hydrotropes are useful for maintaining phase stability, while detergents are useful for cleaning soiled surfaces and to add foaming.

Preferred emulsifiers and detergents are non-ionic alkylated alkoxylate surfactants, preferably polyoxyethylene surfactants. Preferred polyoxyethylene surfactants are alkyl polyoxyethylene surfactants and alkyl aryl polyoxyethylene surfactants. A preferred alkyl polyoxyethylene surfactant which is a detergent is C6-C10 alkyl, 3.5 moles of ethylene oxide (EO) alcohol ethoxylate (AE) sold in association with the trademark Alfonic L610-3.5. Also, preferred alkyl aryl polyoxyethylene surfactants which are emulsifiers are C8 to C16 alkylphenol alkoxylates. These include octyl phenol ethoxylate which is sold in association with the trademark Triton X-405.

The hydrotrope may be an anionic surfactant chosen from alkylated sulfonated diphenyl oxides, alkylated sulfonated diphenyl oxide salts, and mixtures thereof, and preferably is a C6 alkylated sulfonated diphenyl oxide disodium salt.

Typically, the emulsifiers, detergents and hydrotropes are present in a total concentration of about 10 to about 30 parts per hundred parts of hydrogen peroxide or up to about 3 w/w % of the solution. Preferably, they are present in a concentration of from about 0.04 to about 3 w/w %, more preferably from about 0.04 to 2.0 w/w %, and even more preferably from about 0.1 to about 2.0 w/w % of the total solution.

To enhance the marketable qualities of the product, coloring agents or dyes and scents or fragrances (e.g. oxycitrus fragrance) may be added.

In topical solutions, thickening agents (e.g. acrylic and biological polymers), moisturizing and other skin conditioning agents may be added to improve the feel of the product and to prevent drying of the skin.

Corrosion inhibitors may be added to embodiments of the invention for use in cleaning non-ferrous metal substrates. Examples include benzotriazoles (e.g. 1,2,3 benzotriazole, hydrobenzotriazoles, carboxybenzotriazoles), sodium nitrite, sodium molybdate, sodium gluconate, sodium benzoate, and combinations thereof. Corrosion inhibitors may be present singularly or in combination and will typically be present in a concentration of from about 0.05 to about 10 w/w % of the total solution, and preferably from about 0.05 to about 1.5 w/w %.

The present inventive solutions may be applied by spraying, pouring or dipping, or through the use of dispensers, foaming triggers or impregnated cloths.

DETAILED DESCRIPTION OF PREFERRED EMBODIMENTS

Unless the context dictates otherwise, all concentration values are expressed based on the total solution or formulation of the specified embodiment. The term "consisting essentially of" shall be construed to mean, including the listed ingredients and such additional ingredients which do not materially affect the basic and novel properties of the solution or solid formulation (as applicable). The "basic and novel properties" are the bactericidal or virucidal activity of the solution or solid formulation. Also, when used herein, the term "about", when used in connection with a specified value, means that value and such deviations therefrom which do not materially affect the way the solution or solid formulation works. Routine experiments may be performed to determine whether there is a material effect or not. For the sake of clarity, a material effect is an increase or decrease in disinfecting performance of 0.03 $\log_{10}$.

In accordance with the first and second aspects of the invention, the present inventive aqueous solution is made using commercially available hydrogen peroxide solutions sold by Degussa or FMC, for example. Such solutions are typically available as aqueous solutions in a concentration of 35 or 50 w/w %. As discussed in, for example, Kirk-Othmer, "Encyclopedia of Chemical Technology", vol. 13 M. Howe-Grant (ed.) (New York: Wiley-Interscience, 1991) at page 965, these commercial solutions always contain traces of catalytically acting impurities which decompose the hydrogen peroxide, despite appropriate purification measures. Thus, commercial solutions of hydrogen peroxide include stabilizers in small amounts, i.e. measured in parts per million, and have an excellent shelf life. These stabilizers work to deactivate impurities, either by absorption or through the formation of complexes. Known stabilizers for use in stabilizing acidic hydrogen peroxide solutions include organic and inorganic sequestering agents, i.e. stannates and phosphates, and combinations of organic compounds and organometallic salts with or without stannates and phosphates. An exemplary stannate is sodium stannate trihydrate and an exemplary phosphate is sodium pyrophosphate.

Solutions having from about 0.01 to about 1.0 w/w %, especially about 0.5 w/w % hydrogen peroxide are suitable for use as household and commercial disinfectants, bactericides and/or virucides, sanitizers and cleaners. Solutions having about 3 to about 4 w/w % are suitable for use as multipurpose cleaners and bleach alternatives in healthcare facilities, households and commercial facilities. Solutions having about 6 to about 8 w/w % hydrogen peroxide are suitable for use as sporicides, fungicides, virucides and/or bactericides, broad spectrum sanitizers, general purpose cleaners, and bleach alternatives, particularly in institutional, healthcare and food applications, and are suited for multiple level dilution according to the type of disinfection task.

The anionic surfactant enhances the bactericidal and/or virucidal activity of the solution. For bactericidal activity, the C8 to C16 alkyl aryl sulfonic acids and their aforesaid salts are preferred as they are widely available and relatively inexpensive. They are also biodegradable. Preferred alkyl aryl sulfonic acids and their salts are dodecyl benzene sulfonic acid, and tridecyl benzene sulfonic acid and their salts, e.g.

sodium, potassium, ammonium salts. Especially preferred are dodecyl benzene sulfonic acid and alkali metal or ammonium salts thereof.

The C6 to C22 alkyl diphenyl oxide sulfonic acids and alkali metal, ammonium, calcium and magnesium salts thereof have been found to impart virucidal activity to the solution. Preferred members of this class include C6 and C10 alkylated sulfonated diphenyl oxide disodium salts, and dodecyl diphenyl oxide disulfonic acid and disodium 4-dodecylated diphenyloxide sulfonate. The C6 alkylated sulfonated diphenyl oxide disodium salt is perhaps the most preferred.

Of the sulfonated C12 to C22 carboxylic acids and their aforesaid salts, sulfonated 9-octadecanoic acid, disodium 2-sulfo $C_{12}$-$C_{18}$ fatty acid salts and sodium methyl 2-sulfo $C_{12}$-$C_{16}$ esters are preferred.

A preferred salt of naphthalene sulfonic acid is sodium alkyl naphthalene sulfonate.

Preferred salts of C8 to C22 alkyl sulfonic acids are sodium octyl (C8) sulfonate, sodium C14-C17 sec-alkyl sulfonate, and the sodium salts of 1-octane sulfonic acid, 1-decane sulfonic acid, and tridecane sulfonic acid.

Of the aforesaid C8 to C18 alkyl sulfates, sodium lauryl sulfate and sodium octyl sulfate are preferred. In topical solutions, ammonium lauryl sulfate is also preferred.

Of the alkyl or alkenyl esters or diesters of sulfosuccinic acid in which the alkyl or alkenyl groups independently contain from six to eighteen carbon atoms and alkali metal, ammonium, calcium and magnesium salts thereof, disodium lauryl sulfosuccinate and sodium dioctyl sulfosuccinate are preferred in both hard surface and topical solutions. Disodium lauryl ether sulfosuccinate ethoxylated to 3 moles of ethylene oxide is also preferred in topical solutions.

Complex mixtures based on hydrogen peroxide may be unstable, with the hydrogen peroxide concentration diminishing greatly in time due to catalytic decomposition. This may be acceptable in the case of a dry powdered formulation which is used immediately after dissolution in water. However, in the case of aqueous solutions which are not used immediately modifications are required to stabilize or mitigate the decomposition of the hydrogen peroxide. A variety of factors influence the stability of hydrogen peroxide in solutions, including the temperature, the concentration of hydrogen peroxide, the pH value, and above all the presence of impurities with a decomposing effect. We have found that, by the careful selection of the adjuvant materials in the mixture, hydrogen peroxide disinfectant solutions of commercial value can be prepared without the addition of phosphorus-based stabilizers. This is of advantage in jurisdictions which impose restrictions on phosphorus emissions.

A first method of preparing an aqueous acidic solution according to the first and second aspects of the present invention comprises adding the anionic surfactant(s) and optional ingredients such as emulsifiers, detergents, hydrotropes, alcohols, scents, coloring agents, dyes, corrosion inhibitors, naturally occurring carboxylic acids, etc., to distilled water or water purified by other means. A commercially available hydrogen peroxide solution is then added and, if necessary, buffering or other pH adjusting agents are added to achieve the desired pH. A second method involves preparing a powdered formulation by mixing together solid forms of the ingredients of the present solution and then dissolving the powdered formulation in water.

The invention may be better understood by reference to the following examples. The following summary will assist in determining the ingredients of the exemplary solutions.

Hydrogen Peroxide
  The hydrogen peroxide used in all the examples, except for example 10 and 14, is a 50 w/w % technical grade commercial solution manufactured by Degussa containing an effective amount of known stabilizers, estimated at less than 50 ppm. In examples 10 and 14, a 30 w/w % hydrogen peroxide solution sold by Degussa was used.

Anionic Surfactants
  Biosoft S-100™ (DDBSA)=dodecyl benzene sulfonic acid; trademark of Stepan; commercially available as a 98 w/w % solution
  DOWFAX™ hydrotrope=C6 alkylated sulfonated diphenyl oxide disodium salt; trademark of Dow Chemical (this ingredient is also a hydrotrope); available commercially as a 45 w/w % solution
  Dowfax C10L™=C10 linear alkylated sulfonated diphenyl oxide disodium salt; trademark of Dow Chemical; available commercially as a 45 w/w % solution
  Petro ULF™ (ANS)=sodium alkyl naphthalene sulfonate; available commercially as a 95 w/w % solution
  Bioterge PAS-8™ (SOS)=sodium octyl sulfonate; available commercially as a 38 w/w % solution
  Hostapur SAS-30™=sodium C14-C17 sec-alkyl sulfonate; available commercially as a 30 w/w % solution
  Stepanol WAC™ (SLS)=sodium lauryl sulfate; available commercially as a 29 w/w % solution
  Sipon LSB™=sodium lauryl sulfate; manufactured by Henkel; available commercially as a 30 w/w % solution
  Stepanol AM™=ammonium lauryl sulfate; manufactured by Stepan; available commercially as a 30 w/w % solution
  Standapol LF™ (SOS)=sodium octyl sulfate; available commercially as a 35 w/w % solution
  Stepan Mild SL3™ (DSLSS)=disodium lauryl ether sulfosuccinate ethoxylated to 3 moles ethylene oxide (EO); available commercially as a 32 w/w % solution
  Alpha-Step MC-48™ (SMSE/SFA)=solution containing SMSE and SFA (relative ratio of components not given by manufacturer); available commercially as a 37 w/w % solution
  SMSE=sodium methyl 2-sulfo $C_{12}$-$C_{16}$ ester
  SFA=disodium 2-sulfo $C_{12}$-$C_{18}$ fatty acid salt
  Aerosol OT-75™=disodium dioctyl sulfosuccinate; manufactured by CYTEC Inc.; available commercially as a 75 w/w % solution Non-ionic Surfactants
  Surfonic L-610-3™=$C_6$-$C_{10}$ alkyl,3 mole ethylene oxide alcohol ethoxylate; trademark of Huntington
  Alfonic L610-3.5™=$C_6$-$C_{10}$ alkyl, 3.5 moles of ethylene oxide (EO) alcohol ethoxylate (AE); available commercially as a 100 w/w % solution
  Triton X-405™ (OPE)=octyl phenol ethoxylate; trademark of Union Carbide; available commercially as a 70 w/w % solution
  Neodol 91-6™=$C_9$-$C_{11}$, 6 moles of ethylene oxide (EO) alcohol ethoxylate (AE) (about 100% active concentration) manufactured by Shell (for improving wetting and feel)
  Ammonyx LO™=lauramine oxide; manufactured by Stepan (for flash foam stability)

Amphoteric Surfactants
  Mirataine C-30™=cocoamidopropyl betaine; manufactured by Stepan (for flash foam stability); available commercially as a 30 w/w % solution Hydrogen Peroxide Stabilizers Briquest ADPA-60AW™=1-hydroxyethylidene-1,1-diphosphonic acid; trademark of Allbright & Wilson; is available commercially as a 60 w/w % solution Moisturizing Agents glycerin sorbitol Polyquaternium 11™=polymeric quaternary ammonium polymer; manufactured by ISP; available commercially as a 20 w/w % solution Thickening Agents Keltrol RD™=xantham gum; manufactured by Kelco Biopolymers Coloring Agents FD&C Yellow No. 6

Buffering or pH Adjusting agents

NaOH=sodium hydroxide

EXAMPLE 1

Hard surface disinfectant solutions 1a and 1b were prepared as shown in Table 1a below:

TABLE 1a

| INGREDIENT | Solution (w/w %) | |
| --- | --- | --- |
| | 1a | 1b |
| Biosoft S-100 | 0.15 | 0.15 |
| BRIQUEST ADPA-60AW | 0.47 | 0 |
| $H_2O_2$ | 0.60 | 0.60 |
| deionized water | balance to 100 | balance to 100 |
| pH | 1.8 | 1.8 |

Solutions 1a and 1b were tested as specified in American Society of Testing and Materials ("ASTM") standard quantitative carrier test (ASTM Method E2111-00), described in the publication entitled *"Standard Quantitative Test Method to Evaluate the Bactericidal, Fungicidal, Mycobactericidal and Sporicidal Potencies of Liquid Chemical Germicides"*, American Society for Testing of Materials, West Conshohocken, Pa.

The results are shown in Table 1b below:

TABLE 1b

| SAMPLE | Control CFU | Test CFU | Log Reduction |
| --- | --- | --- | --- |
| Solution 1a | $6.76 \times 10^6$ | 0 | 6.76 |
| Solution 1b | $6.76 \times 10^6$ | 0 | 6.76 |

The above results demonstrate that Solutions 1a and 1b are effective in achieving a greater than 6 log reduction in bacterial counts after a three minute contact time.

EXAMPLE 2

Hard surface disinfectant solutions 2a, 2b and 2c were prepared as shown in Table 2 below.

TABLE 2

| INGREDIENT | Solution (w/w %) | | |
| --- | --- | --- | --- |
| | 2a | 2b | 2c |
| Citric Acid | 0.500 | 1.500 | 0.500 |
| Acetic Acid | 1.786 | 0.179 | 0.179 |
| $H_2O_2$ | 1.000 | 1.000 | 1.000 |
| Biosoft S-100 | 0.450 | 0.450 | 0.100 |
| Dowfax Hydrotrope | 0.300 | 0.300 | 0.300 |
| Triton X-405 | 0.044 | 0.044 | 0.044 |
| Surfonic L-610-3 | 0.150 | 0.150 | 0.150 |
| pH | 2.2 | 2.2 | 2.2 |

Solutions 2a, 2b, and 2c were tested using the Gardner scrub test to determine the cleaning efficiency of such solutions as compared to commercially available cleaners, namely Clorox Clean Up™ and 409™. The test procedure is described in the American Society of Testing and Materials ("ASTM") D 4488-85 (Standard guide for testing cleaning performance of products intended for use on resilient flooring and washable walls) but using simulated test soils better representing each application. Solution 2a was tested on kitchen grease, Solution 2b was tested on bathroom soil, and Solution 2c was tested on tea stains. Each of the specified soils was applied to white vinyl tiles. Reflectance measurements were recorded after each stroke of the Gardner scrubber and are plotted in FIGS. 1 to 3.

Figure 2:
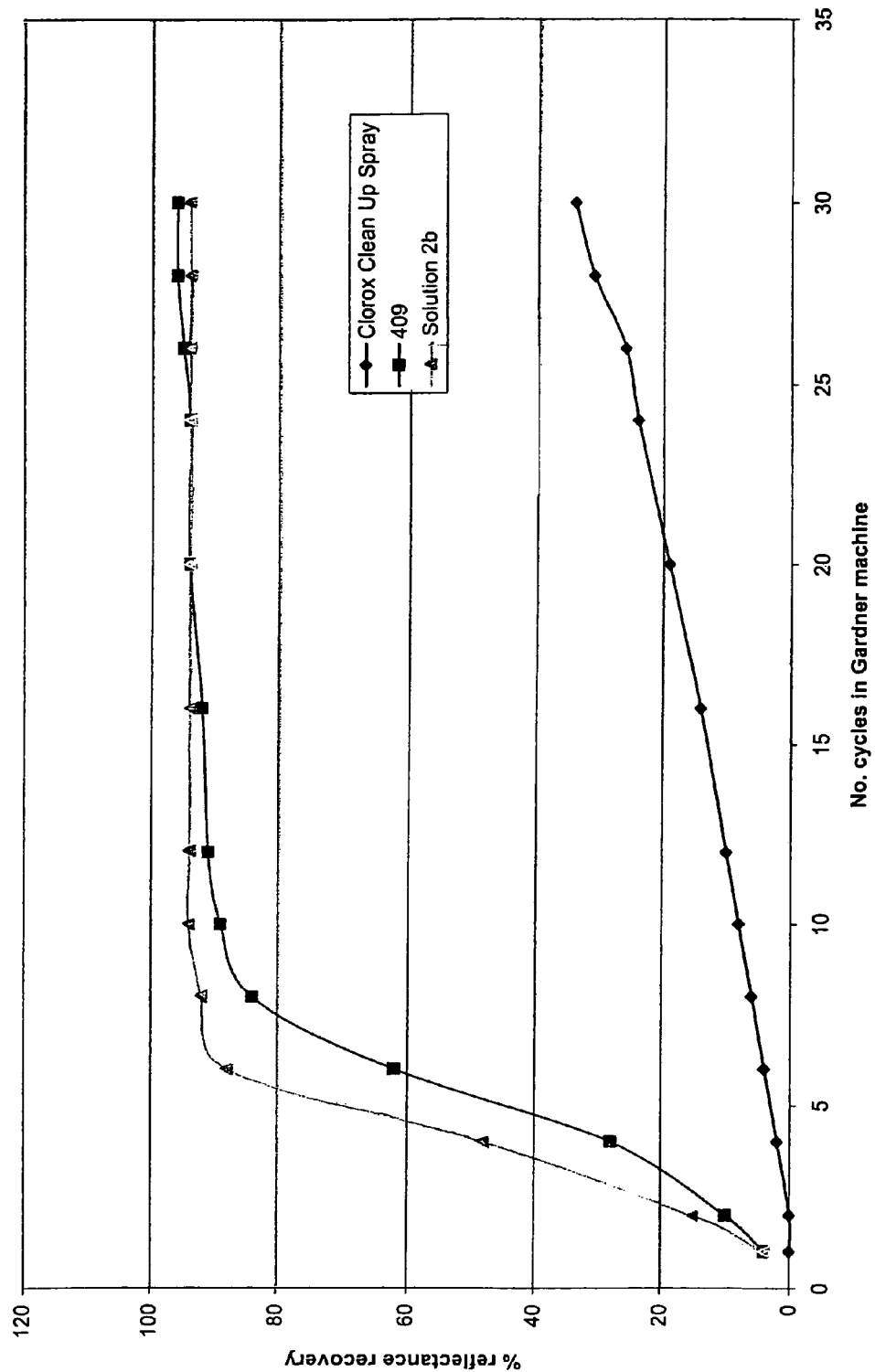
FIG. 2 is a graphical illustration of the cleaning efficiency of Solution 2b, according to another embodiment of the present invention, tested as described in Example 2 below against commercial formulations.
Figure 3:
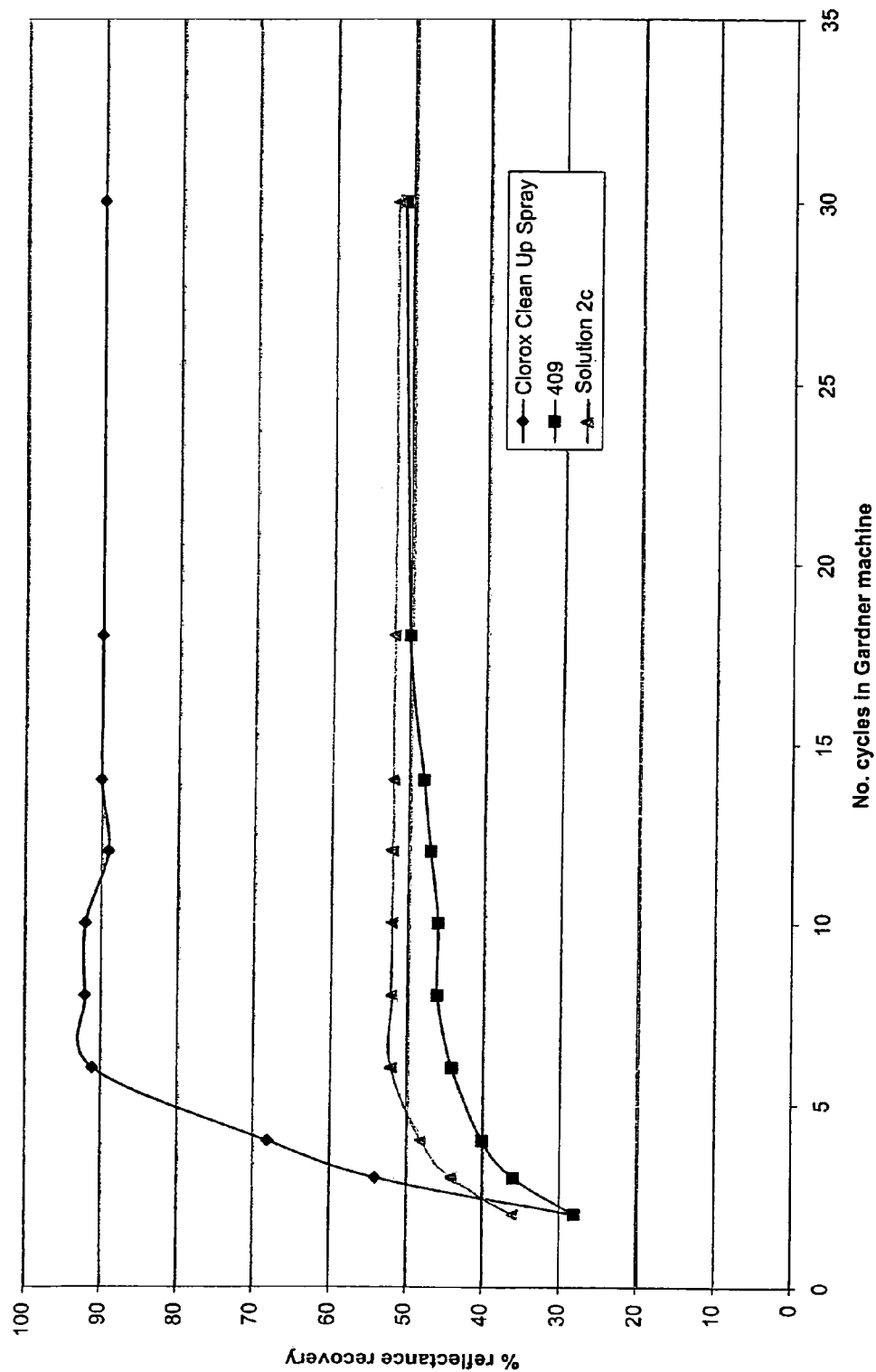
FIG. 3 is a graphical illustration of the cleaning efficiency of Solution 2c, according to yet another embodiment of the present invention, tested as described in Example 2 below against commercial formulations.

FIG. 2 demonstrates that solution 2b is at least as effective as the tested commercial solutions in cleaning bathroom soil. FIG. 3 shows that solution 2c is as effective as 409 in cleaning tea stains. FIG. 1 illustrates that while solution 2a is not as effective as the tested commercial solutions in cleaning kitchen grease, it is nonetheless somewhat effective.

EXAMPLE 3

Hard surface disinfectant solutions 3a and 3b were prepared as indicated in Table 3a below and tested in accordance with the *Official Methods of Analysis* of the Association of Official Analytical Chemists (A.O.A.C.) 16th Edition, 1995 Section 6.3.04, also referred to as the A.O.A.C. Official Method 961.02 titled "Germicidal Spray Products as Disinfectants", Final Action 1964. This method tests the effectiveness of sprays and pressurized spray products as spot disinfectants for contaminated surfaces. The tests used a contact time of 3 minutes against a 5 w/w % soil load of *Staphylococcus aureus* (ATCC No. 6538) and 60 slides. The results are shown in Table 3b below. As shown, none of the 60 slides in each experiment tested positive for the specified organism after being exposed to the test solution.

TABLE 3a

| INGREDIENT | Solution (w/w %) | |
| --- | --- | --- |
| | 3a | 3b |
| $H_2O_2$ | 0.5 | 1.5 |
| Biosoft S-100 | 0.45 | 0.29 |
| Acetic acid | 0.3 | 1 |
| Citric Acid | 0.5 | 0.5 |
| Dowfax hydrotrope | 0.135 | 0.135 |
| Triton X-405 | 0.0443 | 0.0443 |

TABLE 3a-continued

| INGREDIENT | Solution (w/w %) 3a | 3b |
|---|---|---|
| Surfonic L610-3 | 0.15 | 0.15 |
| deionized water | 97.92 | 96.4 |
| pH | 2.2 | 2.2 |

TABLE 3b

Germicidal Test Results

| Test Organism | Solution 3a | Solution 3b |
|---|---|---|
| *Staphylococcus aureus* (ATCC No. 6538) | test not performed | 0/60 |
| *Salmonella choleresuis* (ATCC No. 10708) | 0/60 | 0/60 |

Solutions 3a and 3b were also tested for stability using a hot stability test such as that described in U.S. Pat. No. 5,736,497 to Steiner. The results are summarized in Table 3c below.

TABLE 3c

Stability Test

| | Solution 3a | Solution 3b |
|---|---|---|
| Stability (20 hours @ 97° C.) | 96.4 ± 0.5% | 95.9 ± 0.5% |

The results indicate that upon storage of the solutions at room temperature, more than 95% of the hydrogen peroxide is expected to remain in solution for a period of at least one year.

EXAMPLES 4 to 8

Additional exemplary embodiments of the present inventive solution useful as hard surface disinfectants are summarized in Tables 4 to 8 below.

TABLE 4

| INGREDIENT | Solution (w/w %) 4a | 4b | 4c |
|---|---|---|---|
| Dowfax Hydrotrope | 0.08 | — | 0.08 |
| Biosoft S-100 | 0.18 | 0.18 | 0.18 |
| Triton X-405 | 0.06 | — | 0.04 |
| H$_2$O$_2$ | 1 | 1 | 0.55 |
| pH | 1.91 | 1.97 | 1.91 |
| deionized water | to 100 | to 100 | to 100 |

TABLE 5

| INGREDIENT | Solution (w/w %) 5 |
|---|---|
| Dowfax Hydrotrope | 0.08 |
| Alfonic L610-3.5 | 0.05 |
| Hydrogen Peroxide | 0.55 |
| Biosoft S-100 | 0.18 |
| pH | about 2 |
| deionized water | to 100 |

TABLE 6

| INGREDIENT | Solution (w/w %) 6a | 6b | 6c | 6d | 6e |
|---|---|---|---|---|---|
| Dowfax Hydrotrope | 0.08 | 0.08 | 0.08 | 0.08 | 0.08 |
| Alfonic L610-3.5 | 0.05 | 0.05 | 0.05 | 0.05 | 0.05 |
| Hydrogen Peroxide | 0.55 | 0.55 | 0.55 | 0.55 | 0.55 |
| Dowfax C10L | — | 0.18 | — | — | — |
| Stepan Mild SL3 (SLSS) | — | — | 0.17 | — | — |
| Petro ULF (ANS) | — | — | — | 0.17 | — |
| Stepanol WAC (SLS) | — | — | — | — | 0.16 |
| Biosoft S-100 | 0.18 | — | — | — | — |
| pH | about 2 | about 2 | about 2 | about 2 | about 2 |
| deionized water | to 100 | to 100 | to 100 | to 100 | to 100 |

| INGREDIENT | Solution (w/w %) 6f | 6g | 6h | 6i | 6j |
|---|---|---|---|---|---|
| Dowfax Hydrotrope | 0.08 | 0.08 | 0.08 | 0.08 | 0.08 |
| Alfonic L610-3.5 | 0.05 | 0.05 | 0.05 | 0.05 | 0.05 |
| Hydrogen Peroxide | 0.55 | 0.55 | 0.55 | 0.55 | 0.55 |
| Hostapur SAS-30 | — | — | 0.18 | — | — |
| Standapol LF | — | — | — | 0.18 | — |
| Alpha-Step MC-48 | — | 0.16 | — | — | — |
| Bioterge PAS 8 | 0.17 | — | — | — | — |
| pH | about 2 | about 2 | about 2 | about 2 | about 2 |
| deionized water | to 100 | to 100 | to 100 | to 100 | to 100 |

TABLE 7

| INGREDIENT | Solution (w/w %) 7a | 7b | 7c |
|---|---|---|---|
| Dowfax Hydrotrope | 0.08 | 0.08 | 0.08 |
| Alfonic L610-3.5 | 0.05 | 0.05 | 0.05 |
| Hydrogen Peroxide | 0.55 | 0.55 | 0.55 |
| Biosoft S-100 | 0.18 | 0.18 | 0.18 |
| NaOH (50%) to pH shown | pH 3.8 | pH 5.0 | pH 6.0 |
| deionized water | to 100 | to 100 | to 100 |

TABLE 8

| INGREDIENT | Solution (w/w %) | | | | |
|---|---|---|---|---|---|
| | 8a | 8b | 8c | 8d | 8e |
| Dowfax Hydrotrope | 0.08 | — | 0.08 | 0.08 | 0.08 |
| Alfonic L610-3.5 | 0.05 | 0.05 | — | 0.05 | 0.05 |
| Hydrogen Peroxide | 0.55 | 0.55 | 0.55 | 0.55 | 0.55 |
| Biosoft S-100 | 0.18 | 0.18 | 0.18 | — | 0.18 |
| Phosphoric acid (75%) (for adjusting pH to about 1.8) | 0.06 | — | — | 0.11 | — |
| pH | about 1.8 | about 1.8 | about 1.8 | about 1.8 | about 1.8 |
| deionized water | to 100 | to 100 | to 100 | to 100 | to 100 |

EXAMPLE 9

Hard surface disinfectant solution 9 was prepared as shown in Table 9a below and tested in accordance with ASTM Method E2111-00 (described above) against the polio virus, and in accordance with the A.O.A.C. 960.09 method, titled "Germicidal and Detergent Sanitizing Action of Disinfectants." Final Action A.O.A.C. XV, 1995, Part 6.3.03 (hereinafter referred to as the "A.O.A.C. 960.09 method"), against Staphylcoccus aureus. The A.O.A.C. method is a suspension test standardized b the A.O.A.C., Association of Official Analytical Chemists, which uses a contact time of 30 seconds. The results are shown in Table 9b below.

TABLE 9a

| INGREDIENT | Solution (w/w %) 9 |
|---|---|
| Biosoft S-100 (98% DDBSA) | 2.5 |
| Dowfax C10L (C10 Linear Diphenyl Disulphonate (39%) | 1.0 |
| Alfonic 610-3.5 (Linear Alcohol Ethoxylate (100%) | 0.7 |
| Hydrogen Peroxide (30%) | 3.7 |
| Briquest ADPA-60AW | 0.0 |
| deionized water | 86.8 |
| sulfuric acid | to adjust pH to 0.9 |
| pH | 0.9 |
| Total | 100.0 |

TABLE 9b

| Test Organism (test method) | # of Carriers | Dilution | Contact Temp | Contact Time | CFU/control Carrier | CFU/test Carrier | $Log_{10}$ Red'n |
|---|---|---|---|---|---|---|---|
| Polio Virus (ASTM Method E2111-00) | 6 | 1:16 | room temp. | 5 min. | $8.9 \times 10^3$ | 0 | 3.95 |
| S. aureus (A.O.A.C. 960.09 method) | 6 | 1:64 | room temp. | 30 sec. | $9.4 \times 10^6$ | 12 | 5.88 |

The results indicate that Solution 9 is an effective virucide and bactericide.

Solutions for Topical Application

The hands carry a variety of microorganisms which can be classified as transient or resident. Transient organisms do not grow naturally on the hands, while resident organisms grow naturally on the skin and are harder to remove. The most important transient species are gram negative bacilli such as *Salmonella* spp., *Escherichia coli*, *Pseudomonas aeruginosa*, *Klebsiella* spp., and *Staphylococcus aureus*. Resident organisms consist mainly of *Staphylococcus epidermidis* and other coagulase-negative *staphylococci*, *micrococci*, and *cornynebacteria* (Ayliffe G. A. J., Babb, J. R. and H. A. Lilly, "Tests for Hand Disinfection", Disinfectants: Their use and evaluation of effectiveness, Collins C. H., M. C. Allwood, S. F. Bloomfield and A. Fox (eds), Academic Press, London, UK, 1981). As a consequence, hand washing and disinfection play an important role in biosafety control in the health and dental care, veterinary care, and food handling and processing industries.

In large scale farming operations, animals are typically in close contact with each other and/or with pieces of equipment. Disease-causing organisms are easily transmitted from one animal to another and from equipment to animals. An example of a disease of economic importance is mastitis, which is an inflammation of the mammary glands of bovine species, caused by the presence of bacteria, the most common of which are *Staphylococcus aureus, Streptococcus agalactiae, Streptococcus dysagalactiae* and *Streptococcus uberis*. Mastitis results in lower milk yields and lower mild quality. Thus, its prevention through the combination of therapy and hygiene techniques is of paramount importance. Current prevention techniques consist of spraying, dipping or massaging the udder with a disinfectant liquid in order to maintain the bacterial population numbers under control.

In the control of mastitis, organisms need to be destroyed in very short periods of time, typically no longer than 1 minute, as the disinfectant solution is most easily applied to each animal after it is milked. The disinfecting solution must also be effective against a wide range of gram positive and gram negative organisms, and its activity should not be neutralized by the presence of an organic load. The antimicrobial active should be non-toxic to both the animal and the user, and should not contaminate the milk. Also, the mastitis-prevention composition should not irritate or cause the teat to peel, which will result in udder pain and ultimately affect the milk yield.

The invention provides embodiments which are useful in disinfecting the skin of humans and animals in contact times of less than 1 minute. These embodiments are designed to not only mitigate bacteria, but also to clean the skin without producing adverse effects with frequent use. They are designed to be used as an antimicrobial hand wash for health workers, a surgical scrub solution, a preoperative skin decontamination solution, or a wound cleanser and disinfectant. They may also be used for the periodic treatment of bovine teats for the prevention of mastitis.

In these embodiments, hydrogen peroxide is present in a concentration of between about 0.1 and about 2.5 w/w %, with the preferred range being from about 0.45 to about 1.20 w/w %. Higher concentrations of hydrogen peroxide may result in excessive skin irritation and in some cases temporary whitening of the skin. Lower concentrations of hydrogen peroxide may result in excessively weak biocidal activity, rendering the solution practically ineffective.

The anionic surfactants are preferably chosen from alkali metal, ammonium and ethanolamine salts of dodecyl benzene sulfonic acid, dodecyl sulfate, ethoxylated dodecyl sulfates, dioctyl sulfosuccinates and ethoxylated dodecyl sulfosuccinates. The preferred components are ammonium lauryl sulfate, disodium dioctyl sulfoccinate and disodium lauryl ether sulfosuccinate with 3 moles EO of ethoxylation. These ingredients are present in a total concentration of 0.5 to 8.0 w/w % of the total solution, with the preferred range being between 0.9 to 2.0 w/w %. These selected surfactants do not generally result in excessive drying of the skin or irritation and are preferably used in combination rather than singularly, as this is believed to result in less skin irritation.

The solution may contain a sufficient amount of buffers or other pH adjusting agents to adjust the pH to—and maintain the pH during storage in—the desired range, which is between about 1 and about 4.5, and preferably between about 2.5 and about 4.5. Examples of suitable buffers or other pH adjusting agents include weak organic or inorganic acids, such as citric or phosphoric acids. Alternatively, traditional strong basic pH adjusting agents (e.g. sodium or potassium hydroxide) can also be utilized in order to raise the pH of the mixture to the desired range.

To further enhance the biocidal activity of the solution, benzyl alcohol and/or a short chain $C_2$-$C_6$ alcohol may be utilized in a low enough concentration so as to not render the solution flammable, and to not give rise to a strong alcoholic odor. Particularly preferred short chain alcohols are $C_3$-$C_5$ aliphatic alcohols, and more particularly preferred are n-butanol and n-pentanol in concentrations of between about 2 and about 5 w/w %.

Additional optional ingredients include organic phosphorus-based hydrogen peroxide stabilizers (e.g. solutions sold by Solutia in association with the trade name Dequest™, or by Allbright and Wilson in association with the trade name Briquest™. A particularly preferred example is 1-hydroxyethylidene-1,1-diphosphonic acid available commercially as Briquest ADPA-60AW™ from Allbright and Wilson, or as Dequest 2010™ from Solutia. Of course, if the solution is to be used in jurisdictions which impose restrictions on phosphorus emissions, these ingredients may be replaced with phosphorous free stabilizers such as 8-hydroxyquinoline, stannates, citric acid, nitrilotriacetic acid, and ethylenediamine tetraacetic acid.

The solution may contain skin conditioning and moisturizing agents such as those hydrophobic materials widely known in the art (e.g. glycerin, glycerol, polyquaternium compounds, guar gums, and low hydrophile liyophile balance non-ionic surfactants). Gelling and other viscosity modifying agents can be employed, including cellulosic esters and ethers, acrylic polymers, biological polymers, and sodium chloride in combination with viscosity modifying surfactants. Finally, dyes and fragrances can be utilized to impart color or specific aromas.

The following are examples of embodiments for use in topical applications.

EXAMPLE 10

Four antimicrobial solutions (Solutions 10a, 10b, 11a, and 11b) were prepared and evaluated for use in the control of mastitis. The solutions are summarized in Tables 10a and 11a below. The anionic surfactant Aerosol OT-25 is a disodium dioctyl sulfosuccinate manufactured by CYTEC Inc., while the Sipon LSB is a sodium lauryl sulfate manufactured by Henkel. The nonionic surfactant Neodol 91-6 manufactured by Shell is included for improving wetting and feel. Moisturizing is imparted by glycerin, sorbitol, while the viscosity was raised by using xantham gum (Keltrod RD manufactured by Kelco Biopolymers).

TABLE 10a

Comparative examples of solution for use in the control of mastitis

| | Solution (w/w %) | |
|---|---|---|
| INGREDIENT | 10a | 10b |
| Citric Acid (99%) | 0.05 | 0.05 |
| Briquest ADPA-60AW | 0.05 | 0.05 |
| Aerosol OT-75 | — | 1.00 |
| Sipon LSB | — | 1.00 |
| Neodol 91-6 | — | 0.40 |
| Hydrogen Peroxide (30%) | 1.67 | 1.67 |
| Keltrol RD (xantham gum) | 0.10 | 0.10 |
| Glycerin (99%) | 3 | 3 |
| Sorbitol (99%) | 3 | 3 |
| FD & C Yellow No. 6 | 0.05 | 0.05 |
| NaOH (50%) | qs to pH 4.5 | qs to pH 4.5 |
| deionized water | 86.63 | 84.23 |

TABLE 10b

| Efficacy Data | Solution 10a | Solution 10b |
|---|---|---|
| $Log_{10}$ reduction in the presence of 10% milk; *Staphylococcus aureus* at 30 sec contact time | <3.37 | <5.37 |

Solutions 10a and 10b were evaluated according to a suspension test similar to that described in the A.O.A.C. Method 960.09 (cited more completely above), except that the germicide solution was replaced with a mixture of the germicide solution and milk, at a milk concentration of 10 w/w %. The pass criteria is a $Log_{10}$ reduction of greater than 5.0. Solution 10b is in accordance with the present invention. Solution 10a differs from Solution 10b in that the anionic surfactants were excluded. This experiment demonstrates that the absence of the anionic surfactants (in this case, sodium lauryl sulfate and dioctyl sulfosuccinate) results in a decrease in activity, even in the presence of close to a 2% active concentration of hydrogen peroxide, and an acid pH.

EXAMPLE 11

Solutions 11a and 11b were prepared in accordance to the present invention and summarized in Table 11a below. These solutions contain additional surfactants for improved flash foam for dispensing as a wet foam. In this case, the solutions contain the anionic surfactants ammonium lauryl sulfate (Stepanol AM manufactured by Stepan) and disodium lauryl sulfosuccinate ethoxylated to 3 moles ethylene oxide (EO) (Stepan Mild SL3, manufactured by Stepan). Flash foam stability is provided by the amphoterics, cocoamidopropyl betaine (Mirataine C-30, manufactured by Stepan), and a non-ionic surfactant, lauramine oxide (Ammonyx LO, manufactured by Stepan). Skin emollients are also included, namely glycerin and the polymeric quaternary ammonium polymer, Polyquaternium 11 (manufactured by ISP). The solutions at 55% strength were tested in accordance with the A.O.A.C. 960.09 method and the results are shown in Table 11b below.

TABLE 11a

Efficacy of antimicrobial hand wash solutions

| | Solution (w/w %) | |
|---|---|---|
| INGREDIENT | 11a | 11b |
| Citric Acid (99%) | 0.05 | 0.05 |
| Briquest ADPA-60AW | 0.05 | 0.75 |
| $H_2O_2$ (50%) | 2.0 | 2.0 |
| Glycerin | 3.0 | 3.0 |
| Mirataine C-30 (30% betaine) | 0.6 | 0.6 |
| n-butanol | 4.0 | — |
| Stepanol AM (30% Ammonium LS) | 5.0 | 5.0 |
| Stepan Mild SL3 (32% DSLSS) | 4.0 | 4.0 |
| Ammonyx LO (30% Lauramide oxide) | 0.69 | 0.69 |
| Polyquaternium 11 (20%) | 2.0 | 2.0 |
| pH | 3.0 | 2.5 |
| deionized water | q.s. to 100% | |

TABLE 11b

| | Log Reduction Solution | |
|---|---|---|
| | 11a | 11b |
| Efficacy at a contact time of 30 secs at 55% strength | | |
| Staph. Aureus | >6.00 | >6.00 |
| Escherichia coli | >6.00 | >6.00 |

Solutions 11a and 11b far surpass the requirements of greater than 3-log reduction in the viable numbers of the test organisms at a dilution of 55% and a contact time of 30 seconds.

EXAMPLE 12

Solution 11b was tested further against other organisms cited in the European standard for hand wash disinfection. The method used was the A.O.A.C. 960.09 method modified by replacing the germicide solution with a mixture of the germicide solution and milk, wherein the milk concentration was 10 w/w %. The results shown in Table 12 below demonstrate that this solution conforms to the minimal standards required for antimicrobial hand washes by the European community.

TABLE 12

Efficacy of antimicrobial hand wash per European standard EN 12054

| Test Organism | $Log_{10}$ reduction reduction in the presence of 10% milk; Staphylococcus aureus at 30 sec contact time |
|---|---|
| Pseudomonas aeruginosa | 8.13 |
| Staphylococcus aureus | 7.70 |
| Escherichia coli | 7.64 |
| Enterococcus. hirae | 7.93 |

EXAMPLE 13

Solutions 11a and 11b were evaluated for their irritation to skin according to the OECD standard 404 for measuring skin irritancy of chemicals. The results, and the interpretation of the irritation scores per OECD 404, are included in Table 13 below.

TABLE 13

Irritation indexes compared to commercial antimicrobial hand washes

| Sample | Primary Irritation Index | Response Category per OECD 404 |
|---|---|---|
| Commercial Triclosan-based hand wash | 3.00 | Moderate irritant |
| Solution 11b | 0.58 | Slight irritant |
| Commercial PCMX-based hand wash | 2.25 | Moderate irritant |
| Solution 11a | 0.92 | Slight irritant |

The results show that solutions 11a and 11b, in spite of their strong antimicrobial activity, exhibit milder irritation profiles than currently commercially available products which are based on more traditional antimicrobial agents.

EXAMPLE 14

Solutions 14a, 14b, 14c were prepared in accordance with Table 14a below. These solutions are suitable for cleaning teats of bovine animals and were tested in accordance with the A.O.A.C. 960.09 suspension test method, modified by replacing the germicide solution with a germicide and milk solution, wherein the milk concentration was 10 w/w %. The results, summarized in Tables 14b and 14c below, indicate that the solutions passed this test, as a greater than 5 log reduction in a 30 second contact time was achieved.

TABLE 14a

| | Solution (w/w %) | | |
|---|---|---|---|
| INGREDIENTS | 14a | 14b | 14c |
| deionized water | 83.00 (qs to 100) | | |
| Keltrol RD | 0.10 | | |
| Briquest ADPA-60AW | 0.05 | | |
| Stepanol AM | 0.33 | | |
| Hydrogen Peroxide (30%) | 1.00 | | |
| Glycerol | 3.00 | | |
| Sorbitol | 3.00 | | |
| NaOH | Up to pH = 4.5 | | |
| citric acid | 1.00 | | |
| 1-butanol | 4.00 | 0.00 | 0.00 |
| benzyl alcohol | 0.00 | 3.50 | 2.5 |

TABLE 14a-continued

| | Solution (w/w %) | | |
|---|---|---|---|
| INGREDIENTS | 14a | 14b | 14c |
| Aerosol OT-75 | 0.00 | 0.5 | 0.5 |
| pH | 4.50 | 4.50 | 4.50 |
| Total | 100.00 | 100.00 | 100.00 |

TABLE 14b

The activity against *E. coli* (suspension test method)

| Solution | Dilution | # of Repeats | Contact Time | CFU/ml control | Average CFU/ml test | Average $Log_{10}$ Red'n |
|---|---|---|---|---|---|---|
| 14a | Full Strength | 4 | 30 sec | $0.97 \times 10^6$ | 0 | 5.99 |
| 14b | Full Strength | 4 | 30 sec | $0.97 \times 10^6$ | 0 | 5.99 |
| 14c | Full Strength | 4 | 30 sec | $0.97 \times 10^6$ | 0 | 5.99 |

TABLE 14c

The activity against *S. aureus* (suspension test method)

| Solution | Dilution | # of Repeats | Contact Time | CFU/ml control | Average CFU/ml test | Average $Log_{10}$ Red'n |
|---|---|---|---|---|---|---|
| 14a | Full Strength | 4 | 30 sec | $1.24 \times 10^6$ | 0 | 6.09 |
| 14b | Full Strength | 4 | 30 sec | $1.24 \times 10^6$ | 0 | 6.09 |
| 14c | Full Strength | 4 | 30 sec | $1.24 \times 10^6$ | 0 | 6.09 |

The person skilled in the art will appreciate that many obvious modifications to the above examples may be made without changing the essence thereof. The foregoing description is by way of example only and shall not be construed so as to limit the scope of the invention which is defined by the following claims.

The invention claimed is:

1. An aqueous disinfecting solution having a pH of from about 0.5 to about 6 and consisting essentially of:
   i) hydrogen peroxide in a concentration of from about 0.05 to about 8 w/w % of the total solution;
   ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution; and
   iii) benzyl alcohol in a concentration of from about 0.1 to about 10 w/w % of the total solution.

2. A solution according to claim 1 wherein the solution has a hydrogen peroxide concentration of about 0.05 to about 4 w/w % of the total solution.

3. A solution according to claim 2 wherein the solution has a hydrogen peroxide concentration of about 0.05 to about 2.5 w/w % of the total solution.

4. A solution according to claim 3 wherein the solution has a hydrogen peroxide concentration of about 0.05 to about 1.2 w/w % of the total solution.

5. A solution according to claim 1 wherein the solution has a hydrogen peroxide concentration of about 0.45 w/w % to about 8 w/w % of the total solution.

6. A solution according to claim 1 wherein the anionic surfactant is present in a concentration of about 0.02 to about 2 w/w % of the total solution.

7. A solution according to claim 1 wherein the benzyl alcohol is present in a concentration of about 0.1 to about 5 w/w % of the total solution.

8. A solution according to claim 1 having a pH of about 0.5 to about 4.5.

9. A solution according to claim 1 wherein the at least one anionic surfactant is selected the group consisting of dodecyl benzene sulfonic acid and alkali metal, ammonium, ethanolamine, calcium and magnesium salts thereof, and C6 to C22 alkyl diphenyl oxide sulfonic acids and alkali metal, ammonium, calcium and magnesium salts thereof.

10. A solution according to claim 9 wherein the at least one anionic surfactant is selected from the group consisting of dodecyl benzene sulfonic acid and an alkali metal salt thereof, disodium salt of a C6 alkyl diphenyl oxide sulfonic acid, and disodium salt of a C10 alkyl diphenyl oxide sulfonic acid.

11. A concentrated aqueous hydrogen peroxide solution which produces, when diluted with sufficient amount of water, an aqueous disinfecting solution having a pH of from about 0.5 to about 6 and consisting essentially of:
   i) hydrogen peroxide in a concentration of from about 0.05 to about 8 w/w % of the total solution;
   ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution; and
   iii) benzyl alcohol in a concentration of from about 0.1 to about 10 w/w % of the total solution.

12. A solid disinfectant formulation which produces, when dissolved in sufficient amount of water, an aqueous disinfecting solution having a pH of from about 0.5 to about 6 and consisting essentially of:
   i) hydrogen peroxide in a concentration of from about 0.05 to about 8 w/w % of the total solution;
   ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution; and
   iii) benzyl alcohol in a concentration of from about 0.1 to about 10 w/w % of the total solution.

13. An aqueous disinfecting solution having a pH of from about 0.5 to about 6 and consisting essentially of:
   i) hydrogen peroxide in a concentration of from about 0.05 to about 8 w/w % of the total solution;
   ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution;

iii) at least one additional ingredient selected from the group consisting of a monocarboxylic acid, a polycarboxylic acid, and mixtures thereof, in a concentration of from about 0.05 to about 5 w/w % of the total solution; and iv) benzyl alcohol in a concentration of from about 0.1 to about 10 w/w % of the total solution.

14. A solution according to claim 13 wherein said at least one additional ingredient is present in a concentration of from about 0.05 to about 2 w/w % of the total solution.

15. A solution according to claim 13 wherein the solution has a hydrogen peroxide concentration of about 0.05 to about 4 w/w % of the total solution.

16. A solution according to claim 15 wherein the solution has a hydrogen peroxide concentration of about 0.05 to about 2.5 w/w % of the total solution.

17. A solution according to claim 16 wherein the solution has a hydrogen peroxide concentration of about 0.05 to about 1.2 w/w % of the total solution.

18. A solution according to claim 13 wherein the solution has a hydrogen peroxide concentration of about 0.45 to about 8 w/w % of the total solution.

19. A solution according to claim 13 wherein the anionic surfactant is present in a concentration of about 0.02 to about 2 w/w % of the total solution.

20. A solution according to claim 13 wherein the benzyl alcohol is present is a concentration of about 0.1 to about 5 w/w % of the total solution.

21. A solution according to claim 13 having a pH of about 0.5 to about 4.5.

22. A solution according to claim 13 wherein the at least one anionic surfactant is selected from the group consisting of dodecyl benzene sulfonic acid and alkali metal, ammonium, ethanolamine, calcium and magnesium salts thereof, and C6 to C22 alkyl diphenyl oxide sulfonic acids and alkali metal, ammonium, calcium and magnesium salts thereof.

23. A solution according to claim 13 wherein the at least one anionic surfactant is selected from the group consisting of dodecyl benzene sulfonic acid and an alkali metal salt thereof, disodium salt of a C6 alkyl diphenyl oxide sulfonic acid, and disodium salt of a C10 alkyl diphenyl oxide sulfonic acid.

24. A concentrated aqueous hydrogen peroxide solution which produces, when diluted with sufficient amount of water, an aqueous disinfecting solution having a pH of from about 0.5 to about 6 and consisting essentially of:

i) hydrogen peroxide in a concentration of from about 0.05 to about 8 w/w % of the total solution;

ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution;

iii) at least one additional ingredient selected from the group consisting of a monocarboxylic acid, a polycarboxylic acid, and mixtures thereof, in a concentration of from about 0.05 to about 5 w/w % of the total solution; and iv) benzyl alcohol in a concentration of from about 0.1 to about 10 w/w % of the total solution.

25. A solid disinfectant formulation which produces, when dissolved in sufficient amount of water, an aqueous disinfecting solution having a pH of from about 0.5 to about 6 and consisting essentially of:

i) hydrogen peroxide in a concentration of from about 0.05 to about 8 w/w % of the total solution;

ii) at least one anionic surfactant selected from the group consisting of C8 to C16 alkyl aryl sulfonic acids and alkali metal, ammonium, ethanolamine, calcium and magnesium salts thereof; and C6 to C22 alkyl diphenyl oxide sulfonic acids and alkali metal, ammonium, calcium and magnesium salts thereof; in a concentration of from about 0.02 to about 8 w/w % of the total solution;

iii) at least one additional ingredient selected from the group consisting of a monocarboxylic acid, a polycarboxylic acid, and mixtures thereof, in a concentration of from about 0.05 to about 5 w/w % of the total solution; and iv) benzyl alcohol in a concentration of from about 0.1 to about 10 w/w % of the total solution.

* * * * *